United States Patent [19]
Lipton et al.

[11] 4,350,687
[45] Sep. 21, 1982

[54] PLATELET DERIVED CELL GROWTH FACTOR

[75] Inventors: Allan Lipton, Hershey; Nancy Kepner, Port Royal, both of Pa.

[73] Assignee: Research Corporation, New York, N.Y.

[21] Appl. No.: 234,448

[22] Filed: Feb. 10, 1980

[51] Int. Cl.³ .................. A61K 37/02; C07G 7/00; C12N 5/00; C12P 21/00
[52] U.S. Cl. .................................. 424/177; 435/68; 435/240; 435/241; 260/112 R
[58] Field of Search .................. 435/240, 241, 68; 424/101, 177; 260/112 B, 112 R

[56] References Cited

U.S. PATENT DOCUMENTS 4,261,976 4/1981 Isselbacher et al. ............... 424/95
4,269,825 5/1981 Bohn et al. ........................ 424/85

OTHER PUBLICATIONS

Kohler et al. *Experimental Cell Research* 87 (1974) pp. 297-301.
Kepner et al., Platelets As A Source of Cell-Proliferating Activity *Platelets,* Raven (1978) 205-212.

*Primary Examiner*—David M. Naff
*Assistant Examiner*—Kathleen S. McCowin
*Attorney, Agent, or Firm*—Oblon, Fisher, Spivak, McClelland & Maier

[57] ABSTRACT

A purified cell growth factor is produced which comprises a substantially purified glycoproteinaceous factor from platelets which has mitogenic activity toward transformed cells, a molecular weight of 3,000-5,000 daltons and a pI of 7.8-8.3. The growth factor is stable to treatment with 4M guanidine hydrochloride, and is heat labile when treated at 100° C. for 5 minutes.

17 Claims, 6 Drawing Figures

PLATELET DERIVED CELL GROWTH FACTOR

BACKGROUND OF THE INVENTION

1. Field of the Invention

The present invention relates to a tumor specific, mitogenic growth factor from platelets, its purification, and its uses.

2. Description of the Prior Art

Cultivation of most mammalian cells as currently practiced in vitro requires a complex mixture of nutrients, including macromolecules of unknown structure isolated from biological sources. Presently, cell lines are grown in media containing serum, and particularly those which contain fetal calf serum. However, the relative scarcity and expense of fetal calf serum has led to the investigation of other media in which serum is not required. In addition, since the exact nature of all components in serum is unknown, it has been impossible to specify exactly which components are required for growth of cells. Accordingly, attempts to study cell growth have been hampered by the lack of growth media having a defined composition.

Various studies have shown that, in addition to simple nutrients necessary for the growth of any simple organism, differentiated cells such as tissue cells require more complex substances for growth or cell division, presumably synthesized by other parts of the organism in which the tissue is found. These substances, whose structures are generally unknown, are referred to as growth factors.

Previous work in this area has shown that growth factors present in blood serum promote the multiplication and survival of certain cultivated cells, such as 3T3 mouse fibroblasts. Various growth factors have been isolated which are indicated to be of use in promoting cell division of non-transformed, i.e., normal, cells: for example, a growth-promoting polypeptide isolated from blood serum and disclosed in U.S. Pat. No. 4,054,557. However, also desirable are growth factors for transformed cells, i.e., those cells that have been converted by a viral or chemical agent into a tumor-like cell line. Such cells no longer grow in orderly fashion in cell cultures and result in tumors when injected into animals. Isolation of tumor-specific growth factors would aid in the study of in vivo and in vitro tumor growth and be of benefit in the clinical treatment of tumors.

One evident source of cell growth factors is blood serum, since blood serum itself will support cell growth in vitro. Blood serum, the liquid fraction of blood that remains after clotting, has been used as a major component of tissue culture media. Blood plasma, the liquid fraction of blood that has not been allowed to clot, has been shown to be less effective than serum in promoting the growth of various tissue culture lines, such as chicken or mouse fibroblasts. Plasma does, however, allow for the survival of cells without an increase in their cell number.

Accordingly, it has been postulated that a serum mitogenic (cell division) factor, or factors, is released from precursors in plasma or from platelets (thrombocytes) when blood is clotted in the preparation of serum. This hypothesis has been tested in previous studies by both of the present inventors, some of which are reported in Kohler and Lipton, Experimental Cell Research 87 (1974) 297–301 and Kepner, Creasy, and Lipton, "Platelets as a Source of Cell-Proliferating Activity" in Platelets, de Gaetano and Garattini, eds., Raven Press, N.Y. (1978), which are hereby incorporated by reference. Serum and plasma were separately fractionated on Sephadex G-100 columns at pH 7.4 and pH 2. Sephadex is a bead-formed gel prepared by cross-linking dextran with epichlorohydrin. Sephadex G-100 comprises beads of 40–120 $\mu$m diameter (dry) and having a pore size selective for peptides and globular proteins in the molecular weight range of 4,000 to 150,000 daltons and dextrans in the range 1,000 to 100,00 daltons.

The growth promoting activity for 3T3 mouse fibroblasts from rat serum and plasma appeared to be eluted at the same time from each column. There was, however, a greater stimulation of cell growth with serum eluent than with plasma eluent. The growth promoting factor(s) found in plasma appeared to be similar in molecular weight to that found in serum. Therefore, it did not appear that the serum growth factor was the product of degradation of a precursor of higher molecular weight present in plasma. It seemed likely that the mitogenic activity for 3T3 cells found in serum was instead released from platelets during the clotting process. This work was reported in Kohler and Lipton, Experimental Cell Research 87 (1974) 297–301.

Platelets were next shown to be a direct source of mitogenic activity. Human platelet extracts were made by freezing and thawing the cells six times in glass tubes to disrupt the platelets. The platelet extract prepared in this fashion stimulated the growth of 3T3 cells approximately 5-fold more than an equivalent amount of serum. This same platelet extract was also used in a culture medium for SV3T3 cells, mouse fibroblasts that had been transformed by Simian virus into a tumor-like cell line. There appeared to be little difference in stimulation for this cell line between the human platelet extract and human serum, an indication that the extract at this stage was not specific for tumors. This initial platelet extract was designated $PDGF_1$, (platelet derived growth factor for non-transformed cells), and is described in Kohler and Lipton, Experimental Cell Research 87 (1974) 297–301.

In an attempt to isolate growth factors specific for tumors, other extraction techniques were tried with platelets. Mitogenic activity for SV3T3 cells could be obtained by washing outdated human platelets with physiological saline or by incubating thus washed platelets with $10^{-8}$ M ADP (or thrombin or N-ethylmaleimide) in the absence of plasma and calcium. Unlike the original frozen and thawed extracts, both platelet saline wash and ADP treated platelet supernatants (ADP released factor) were more active than serum in promoting the growth and survival of SV3T3 cells.

Gel filtration of either the saline wash material or the ADP release factor on Sephadex G-100 at pH 7.4 yielded a stimulating fraction for SV3T3 cells having a molecular weight of approximately 72,000 daltons and an isoelectric point of approximately 10–10.5. Activity was lost when the platelet extracts were treated with periodate, indicating the presence of a glycoprotein. This factor was designated $PDGF_T$ (platelet dependent growth factor for transformed cells) and is described in an article by Kepner, Creary, and Lipton in Platelets, de Gaetano and Gasattini, eds. Raven Press, N.Y. (1978) p. 205–212. However, this platelet extract represents only a 1- or 2-fold purification over serum, and, accordingly, does not represent a desirable agent for use in a purified, tissue-cell growth medium. In the process of working toward isolation of a pure growth factor, the present invention was made.

SUMMARY OF THE INVENTION

Accordingly, it is an object of this invention to provide a purified growth factor selective for transformed cells.

It is a further object of this invention to provide a method of purifying a growth factor from platelets that is selective for transformed cells.

These and other objects of the invention as will hereinafter become more readily apparent have been accomplished by providing a purified cell growth factor comprising a substantially purified glycoproteinaceous factor from platelets which has mitogenic activity toward transformed cells, a molecular weight of 3,000–5,000 daltons, a pI of 7.8–8.3, which is stable to treatment with 4 M guanidine hydrochloride, and which is heat labile when treated at 100° C. for 5 minutes.

BRIEF DESCRIPTION OF THE DRAWINGS

A more complete appreciation of this invention and many of the attendant advantages thereof will be more readily obtained as the same becomes better understood by reference to the following detailed description when considered in connection with the accompanying drawings, wherein.

DESCRIPTION OF THE PREFERRED EMBODIMENTS

The present invention provides a growth factor (mitogenic factor) that is specific for transformed cells and which has been isolated from platelets. This platelet dependent growth factor ($PDGF_2$) has a molecular weight of from 3,000–5,000 daltons and a pI of 7.8–8.3, indications that this factor is different from $PDGF_T$. $PDGF_2$ is stable to treatment with 4M guanidine hydrochloride, is heat labile (inactivated at 100° C. after 5 minutes), and has mitogenic activity that is partially destroyed by trypsin and completely destroyed by periodate. This and other data indicate that the factor is at least partially a glycoprotein.

The following table indicates the differences between $PDGF_2$ and other previously developed growth factors derived from platelets:

|  | $PDGF_1$ | $PDGF_T$ | $PDGF_2$ |
| --- | --- | --- | --- |
| Stable to heat (100° C.) | yes | no | no |
| structure destroyed by exposure to 4M guanidine hydrochloride | ? | yes | no |
| isoelectric point | 9.6–10.2 | 10–10.5 | 7.8–8.3 |
| molecular weight | 15–20,000 | 72,000 | 3–5,000 |
| affinity for DEAE Sephacel | no | ? | yes |
| promotes 3T3 cell division | yes | no | no |
| promotes SV3T3 cell division | no | yes | yes |
| Specific activity for SV3T3 cell division (per μg) | ? | 1 | 100 |

? - indicates that this information is not currently known.

The general technique for the partial purification of the mitogenic factor for transformed cells from human fibroblasts is as follows: Platelets from any mammalian source may be used. Human and bovine platelets are preferred. Most preferred are human platelet concentrates used within 6 weeks of their becoming unfit for transfusion. Platelets are washed from one to ten times with isotonic saline or any other aqueous solution of equal ionic strength. Preferred are 3–8 washings and most preferred are about 5 washings. Wash solutions may be at any temperatures below 24° C. at which the wash solution is still fluid. Preferred are solutions between 10° and 24° C. and most preferred are solutions at about 18° C. This washing removes any mitogenic activity present in the plasma bathing the platelets. Some mitogenic activity for 3T3 and SV3T3 cells is usually present in the first saline wash and is probably released from the platelet during collection or storage. Platelets washed as many as 15 times with isotonic saline do not release any more activity. These washed platelets are next incubated in isotonic saline or another aqueous solution of equal ionic strength in the absence of plasma and calcium. The duration of the incubation is not critical although very short incubations do not release all of the growth factor present in the platelets. Incubation longer than 10 minutes are preferred. Incubations of about 30 minutes appear to be a suitable compromise between shorter incubations that do not release all the growth factor and longer incubations which require undue time and as such are preferred. Suitable incubation times are inversely related to incubation temperatures in a general way, as is well understood in this art.

Incubations may occur at any temperature at or above 25° C. and below temperatures at which this growth factor is destroyed. The upper limit depends on both temperature and length of incubation as is well known in the art, and can be easily established by simple experimentation for any given incubation period. For example, $PDGF_2$ activity is known to be destroyed by heating at 100° C. for 5 minutes. Preferred incubation temperatures are between 25° C. and 40° C. Most preferred are temperatures of about 37° C.

The platelets are removed from the normal saline by centrifuging at above 12,000 g for sufficient time to cause platelets to settle to the bottom of the centrifugation tube, preferably for about for 30 minutes at about 16,000 g (particularly when using isotonic saline). The supernatant can be lyophilized and stored frozen if desired (crude platelet extract).

Several growth factors are present in this crude platelet extract. This was initially indicated by the effects of heat on the ability of the crude extract to provide cell division. Growth promoting activity for 3T3 cells ($PDGF_1$) is stable on heating to 100° C. for 5 minutes.

In contrast, growth promoting activity for SV3T3 cells from platelet extracts ($PDGF_T$) is destroyed by heating at 100° C. for 5 minutes.

These factors can be partially separated on a Sephadex G-100 column at pH 7.4. The impure factor that can selectively promote the growth of SV3T3 cells ($PDGF_T$) appears to have a molecular weight of approximately 72,000 daltons. Later findings indicate this is not the actual growth factor. One possible explanation now appears to be that $PDGF_2$ may be attached to a larger "carrier protein" to form $PDGF_T$, although the exact structure of $PDGF_T$ is not known. However, even at this stage of purification the effects of $PDGF_T$ appear to be quite specific in that $PDGF_T$ fractions do not promote the growth of 3T3 cells (non-transformed cells).

The impure platelet factor that promotes the growth of SV3T3 cells ($PDGF_T$) is split into fragments by exposure to 4 M guanidine hydrochloride. These fragments are different from both $PDGF_T$ and $PDGF_2$, having a higher molecular weight than $PDGF_2$. The mitogenic activity of $PDGF_T$ is destroyed by treatment with sodium periodate (0.05 mM at 4° C. for 48 hours) and is partially destroyed by trypsin treatment (5 mg insoluble trypsin/2 ml crude platelet extract incubated 6 hours at 37° C.). It would thus appear that mitogenic activity for SV3T3 cells and other transformed cells from human platelets is due to a glycoprotein.

Further purification of $PDGF_T$ (or crude platelet extract) from platelets gives the purified growth factor $PDGF_2$. Either crude platelet extract or $PDGF_T$, preferably crude platelet extract, is adsorbed on a cellulose-based ion exchanger, preferably having a bead-formed gel-like structure strengthened by cross-linking with epichlorohydrin and having dialkylaminoalkyl hydrochloride ion-exchanging groups. Most preferred is a DEAE Sephacel column. Suitable pH ranges for adsorption are pH 5–9, most preferably about pH 8. The ion exchange resin is then eluted with a salt solution, preferably Tris HCl or sodium chloride, of either constant or increasing gradient concentrations, most preferably a sodium chloride gradient from 0.01 M to 0.12 M.

Isoelectric focusing of the fractions having SV3T3 activity (now identified as $PDGF_2$) indicates a pI of 7.8–8.3, compared to 10–10.5 for $PDGF_T$. Additionally, the molecular weight $PDGF_2$ apears to be much lower, about 3,000–5,000 for $PDGF_T$ compared to about 72,000 for $PDGF_T$. Other distinguishing characteristics include an activity of $PDGF_2$ about 100 times greater than that of $PDGF_T$. In addition, $PDGF_2$ is stable on exposure to 4 M guanidine hydrochloride.

In another purification technique, $PDGF_T$ can be adsorbed on lectin-coated surface, preferably a lectin that binds α-D-mannopyranose, α-D-glucopyranose, D-fructofuranose, their glycosides, and sterically related structures. The most preferred lectin is concanavalin A (Con A). The lectin may be coated on or covalently bound to sepharose or any other inert matrix that will accept ConA-like substances. Most preferred is a Con-A-Sepharose column. Mitogenic activity can be eluted by any non-interfering element capable of replacing adhered glycoproteins from lectins, preferably methyl-α-D-glucopyranose. The fractions having mitogenic activity for SV3T3 cells were shown to have the same pI, molecular weight, and specific activity as $PDGF_2$ from the Sephacel column discussed above, and are accordingly also designated $PDGF_2$.

Many applications for $PDGF_2$ appear possible. One such use is the replacement of serum and other growth promoting factors in the in vitro growth of human and animal tumors. At the present time, human tumor stem cells are grown by incorporating feeder layers of spleen cells plus high concentrations of serum into a bottom layer of 5% agar and a top layer of 3% agar. $PDGF_2$ can be incorporated directly into the agar so as to replace both the spleen cell feeder layer and the serum supplement. It should thus be possible to grow tumor cells in a defined medium that contains $PDGF_2$ as the only (or the major) protein source. This will allow the performance of many experiments that seek to study the effect of the other macromolecules without the interference of either feeder layers or of all the proteins present in human serum. Thus a more defined or "clean" system will be available. $PDGF_2$ could be added to any presently available medium to replace serum in compositions now requiring serum. The amount of $PDGF_2$ required depends on the medium and the cell line chosen as is well known in the art and could be determined easily by simple experimentation.

Having generally described the invention, a more complete understanding can be obtained by reference to certain specific examples, which are provided herein for purposes of illustration only and are not intended to be limiting unless otherwise specified.

EXAMPLES

The examples cited herein describe the characterization of $PDGF_2$, methods for its purification, and its effect on various cell lines.

CELLS AND GROWTH MEDIA

Swiss 3T3 and SV3T3 cells were obtained from Dr. Marquerite Vogt and Dr. Renato Dulbecco, Salk Institute, San Diego, Ca. A31-714. These cell lines are described in Watkins, J. F. and Dulbecco, R. *Proc. Natl. Acad. Sci. U.S.*, 58, (1967) 1396–1403. NQ-T-1 cells were obtained from Drs. J. DiPaola and T. Kakunaga of the National Cancer Institute, Bethesda, Md. These cell lines are described in DiPaolo and Kakunaga, *Internat. J. of Cancer* 12 (1073) 463–473. K16 and W8 cells were obtained from Dr. Bernard Weinstein, Columbia University, New York City and are described in Yamaguchi, M. and Weinstein, B., *Proc. Natl. Acad. Sci. U.S.*, 71, (1974) 214–218.

The cells were routinely cultured in Dulbecco and Vogt's modification of Eagle's medium (GIBCO) in the presence of 10% fetal calf serum (FCS). The cells were transferred with the use of $Ca^{2+}$ and $Mg^{2+}$ free 0.3% trypsin solution containing 0.14 M NaCl 2 mM KCL, 4 mM $Na_2HPO_4$ and 5 mM dextrose. After centrifugation, the cells were plated at the appropriate density in 60 mm Falcon plastic dishes.

STANDARD ASSAY FOR GROWTH FACTOR

3T3 and SV3T3 cells ($10^5$) were plated in 0.4 and 0.15% FCS respectively and cultures were incubated in 12% $CO_2$ at 37° C. A31-714 and NQ-T-1 cells ($10^5$) were plated in media containing 0.4 and 0.1% FCS respectively and cultures were incubated in a 7% $CO_2$ incubator. K-16 and W8 cells were cultured in media containing 0.6 and 0.3% FCS respectively in a 7% $CO_2$ incubator. This concentration of serum did not induce a significant increase in cell number per dish over a period of 4 days. The sample to be tested was added after 2–4 hours incubation on day 1. Number of cells were determined in a Coulter counter 4 days after the start of the experiment. Net cell count was obtained by subtracting the number of cells in control plates (no additions) after 4 days incubations. All cell counts were performed in duplicate; all experiments were repeated at least twice.

EXPERIMENTAL PROCEDURE

As a source of the various growth factors, human platelet concentrates stored at room temperature were used within six weeks of their becoming unfit for transfusion. Platelets were washed at least five times with 0.85% sodium chloride at 18° C. Washing removed any mitogenic activity present in the plasma bathing the platelets. Some mitogenic activity for the 3T3 and SV3T3 cells was usually present in the first sodium chloride wash and was probably released from the platelets during collection or storage. Platelets washed as many as fifteen times with 0.85% sodium chloride did not release any more activity. When these washed platelets were incubated in 0.85% sodium chloride for 30 minutes at 37° C. in the absence of plasma and calcium, mitogenic activity for both cell types was obtained. In all experiments described below, "crude platelet extract" was made by incubating platelets (washed five times) for 30 minutes at 37° C. Crude platelet extract obtained in this fashion was approximately 20 times more effective than Fetal Calf Serum (FCS) in promoting the growth of SV3T3 cells.

Figure 1:
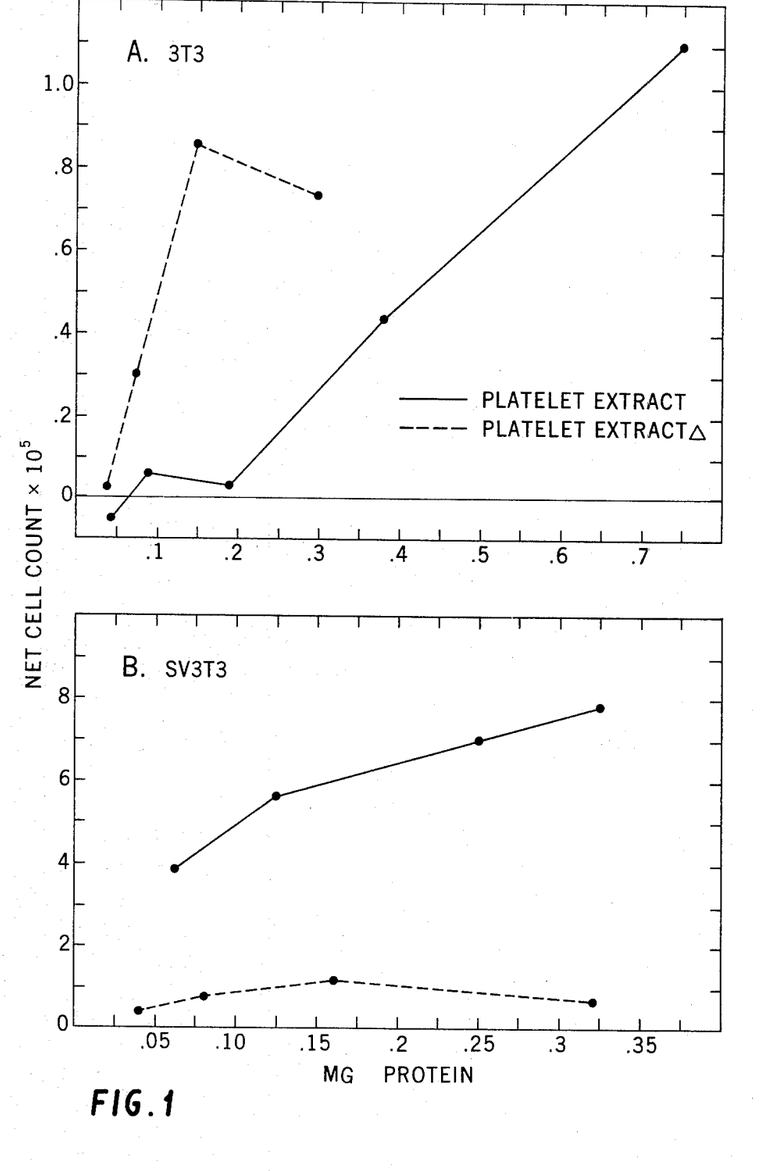
FIG. 1 shows heat sensitivity of mitogenic activity for 3T3 and SV3T3 cells from human platelets.

The first evidence that there might be several factors present in platelet extracts came from preliminary attempts to charcterize the platelet mitogen. Growth promoting activity in crude platelet extracts for 3T3 cells ($PDGF_1$) was stable on heating to 100° C. for 5 minutes. In contrast, $PDGF_T$ was destroyed by heating to 100° C. for 5 minutes. An experiment showing heat sensitivity is shown in FIG. 1. Thirty to eighty units of outdated human platelet concentrates were pooled and spun at 163 g for 10 minutes to remove RBC's. They were respun at 5875 g for 10 minutes. The platelet bottom was washed and centrifuged 5 times at 5875 g. Each wash was with 400–800 ml. isotonic saline. The final platelet button was resuspended in 40–80 ml. isotonic saline. Washed platelets were released by incubation at 37° C. for 30 minutes, then centrifuged, and the supernatant (crude platelet extract) sterilized. $PDGF_2$ can also be released from platelets by treatment with thrombin, collagen, freezing and thawing, N-ethylmaleimide, arachidonic acid, or any other method of inducing the platelet release reaction [Linder, B. L., Chernoff, A., Kaplan, K. L., and Goodman, D. S. Proc. Natl. Acad. Sci. USA 76; 4107–4111, 1979; Holmsen, H. Day, H. J., and Stormorkken, H. Scand, J. Haemat; Suppl. 8, 1969; and Holmsen, H. Advances in Pharmacology and Therapeutics p. 175-204 Ed. Vargaftig. 1978]. The extract was divided into two equal portions and half was heated at 100° C. for 5 minutes and then centrifuged. Both samples (heated and non-heated) were sterilized using millipore filters (0.22$\mu$). Growth promoting activity in crude platelet extracts for 3T3 cells ($PDGF_1$) was stable on heating to 100° C. for 5 minutes. In contrast, growth promoting activity for SV3T3 cells in crude platelet extracts ($PDGF_T$) was destroyed by heating at 100° C. for 5 minutes.

These factors can be partially separated on a Sephadex G100 column at pH 7.4. The impure factor that can selectively promote the growth of SV3T3 cells ($PDGF_T$) appears to have a molecular weight of approximately 72,000 daltons. Its effect appears to be quite specific in that fractions do not promote the growth of 3T3 cells. Twenty-five to fifty percent of the growth promoting activity for SV3T3 cells was recovered from Sephadex columns, while only about 10% of growth promoting acxtivity for 3T3 cells originally present in platelet extracts was recovered.

Figure 2:
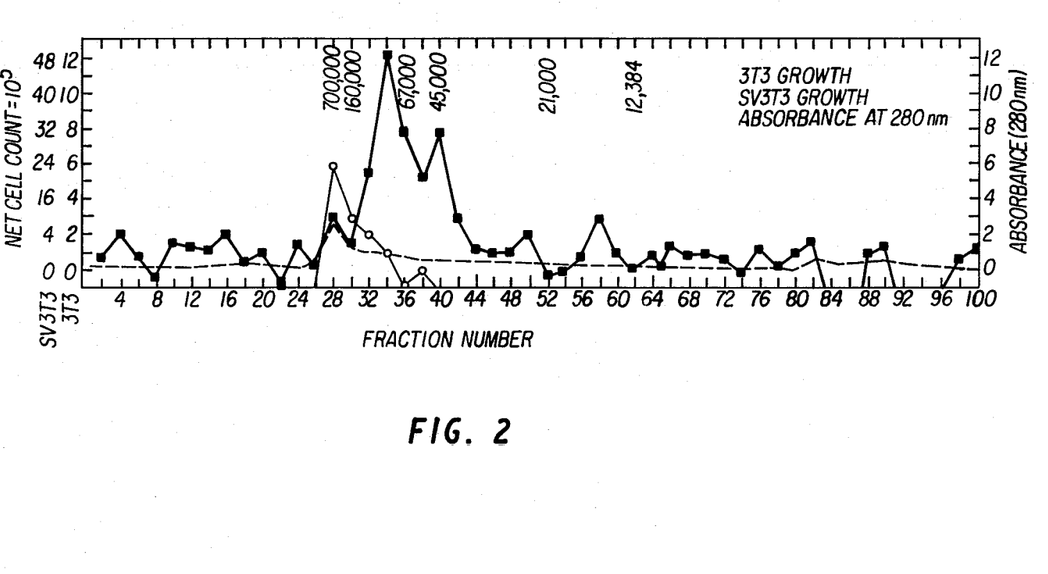
FIG. 2 shows sephadex G100 gel filtration of extract from human platelets.

An example of Sephadex G100 gel filtration is shown in FIG. 2.

Platelet extracts were prepared as described above. Six mls. of extract were placed on a Sephadex G-100 column 0.01 M Tris-HCL pH 7.4. Fractions were eluted in 5 ml volume from a 3×80 cm. column at 4° C. The standard growth assay for SV3T3 cells was performed as described in Materials and Methods section using 0.5 ml of each column fraction. $PDGF_2$ can be purified from $PDGF_T$ fractions or from crude platelet extract by chromatography on Con A-Sepharose. Crude platelet extract was prepared as described above, sterilized using a 0.22$\mu$ Millipore filter, and lyophilized. This material was reconstituted in an equal volume of 0.01 Tris-0.01 M NaCL, pH 8.0. Six ml of platelet extract was placed on a 1×5 cm Con A-Sepharose column, 0.01 M Tris-0.01 M NaCL, pH 8.0 at 4° C. After 100 ml were collected, a step-wise gradient using 0.05, 0.1, 0.2, 0.4 and 1 M methyl-$\alpha$D-glucopyranoside as indicated was employed. 2.5 ml fractions were collected and sterilized. 0.3 ml from each column fraction was added to SV3T3 cells in the standard growth assay described above.

Figure 3:
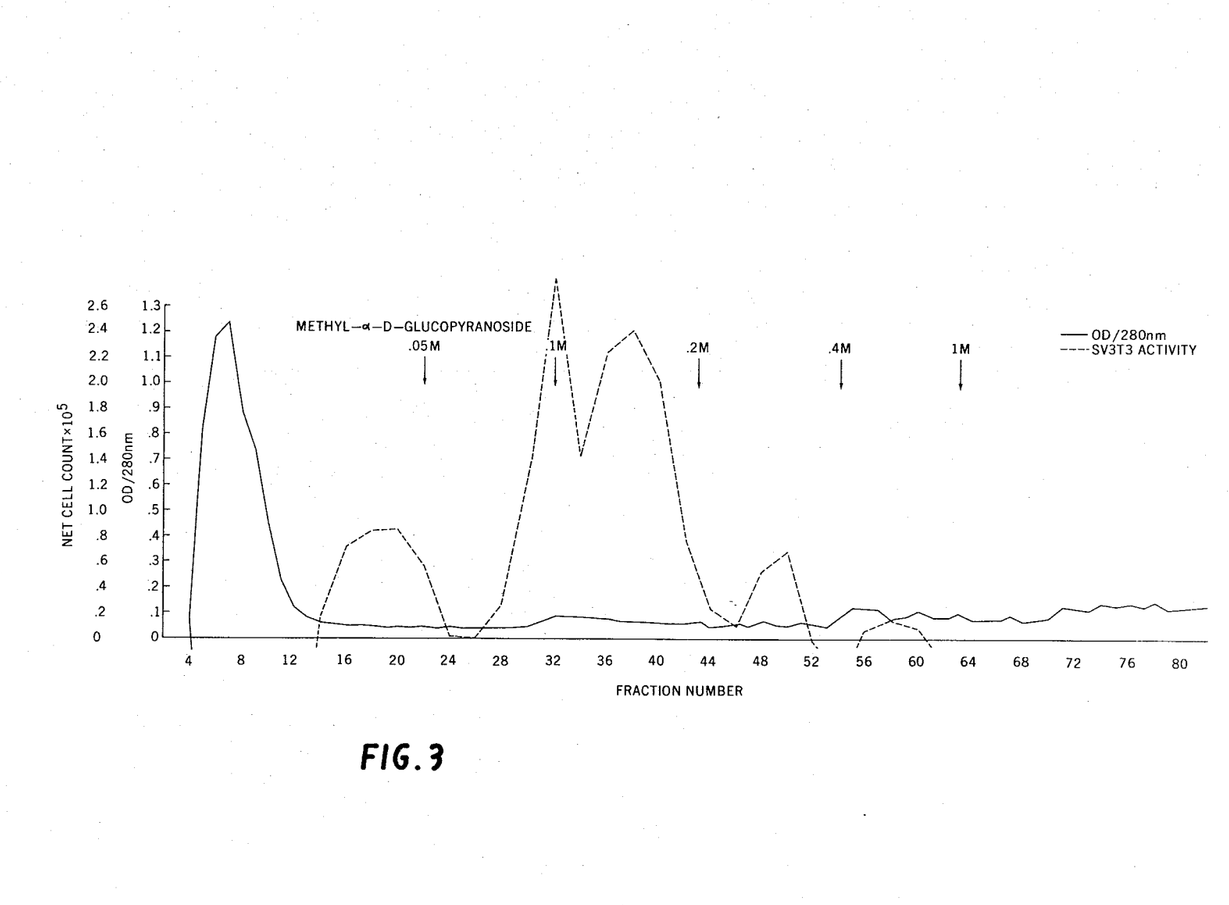
FIG. 3 shows Con A-Sepharose chromatography of extract from human platelets.

FIG. 3 shows the results of the preceeding experiment. The active fractions were approximately 100 times more active than FCS in promoting SV3T3 growth. Ninety-five percent of the original activity was recovered from this Con-A-Sepharose column. (Concanavalin A binds gluco- and mannopyranosides as well as a variety of glycoproteins).

Figure 4:
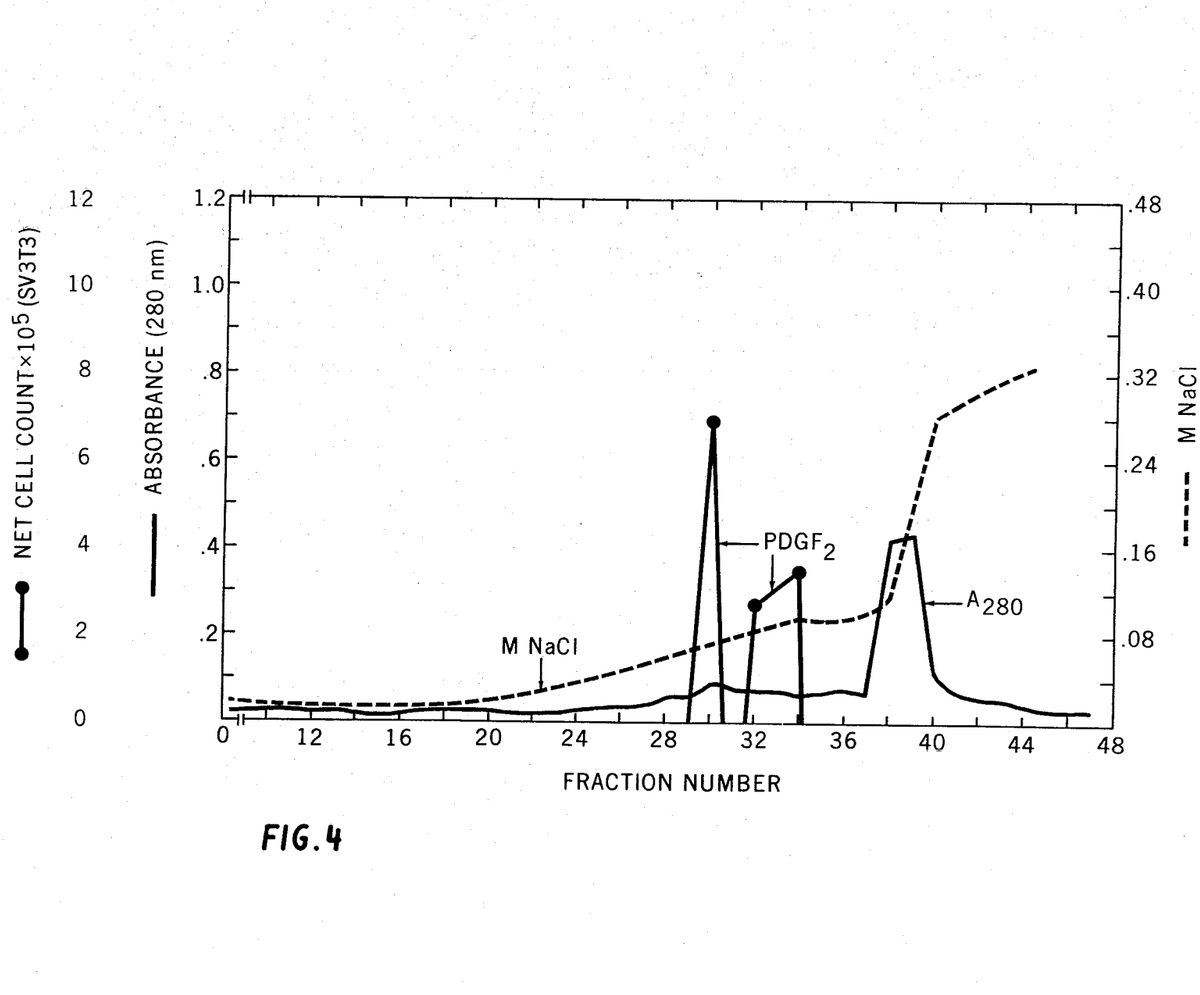
FIG. 4 shows DEAE-Sephacel chromatography of extract from human platelets.

$PDGF_2$ can also be purified from $PDGF_T$ fractions or from crude platelet extract by chromatography on DEAE-Sephacel. Crude platelet extract was prepared as described above. Six ml of extract were dialyzed in 0.01 M Tris HCL-0.01 M NaCL buffer pH 8.0, and then placed on a 1.5×25 cm DEAE-Sephacel (Pharmacia) column with the same buffer at 4° C. After 100 ml were collected, a NaCL gradient (0.01–0.16 M) of 100 ml was used to elute the $PDGF_2$ activity. The column was finally washed with 0.5 M NaCL to remove any remaining protein. Five ml fractions were collected and sterilized using 0.22$\mu$ Millipore filters. 0.5 ml of each column fraction was added to the standard growth assay for SV3T3 cells.

FIG. 4 shows the results of the preceeding experiment. The active fractions were approximately 100 times more active than FCS in promoting SV3T3 growth. Twenty-five percent of the original activity was recovered from this column.

$PDGF_2$ has been characterized by isoelectric focusing and its molecular weight determined by means of ultragel filtration.

Figure 5:
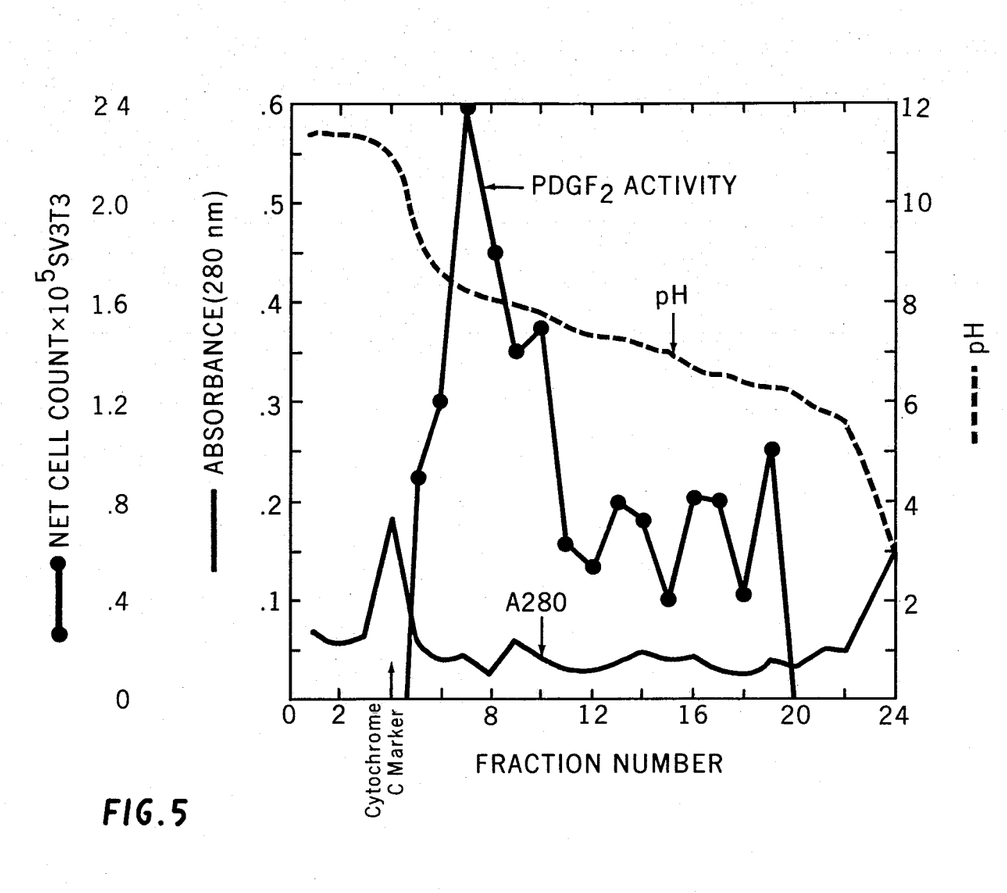
FIG. 5 shows preparative isoelectric focusing of $PDGF_2$ from DEAE-Sephacel column.

In one experiment, 4 ml of $PDGF_2$ activity from a DEAE-Sephacel column were dialyzed in 1% glycine and focused on an LKB electrofocusing column (110 ml) pH range 7–10, was used; cytochrome C with a pI of 10.6 was used as a marker. The samples to be tested were collected in 5 ml fractions, dialyzed with 0.85% NaCL to remove sucrose and sterilized using 0.22$\mu$ Millipore filters. 0.5 ml of each fraction was added to the standard growth assay for SV3T3 cells.

FIG. 5 shows the results of this experiment. The SV3T3 growth promoting factor (PDGF$_2$) is recovered between pH 7.8–8.3.

Figure 6A:
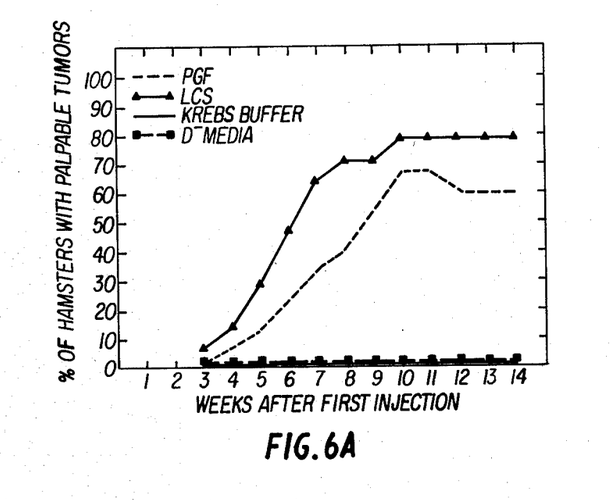
FIG. 6 shows tumor growth in hamsters innoculated with Herpes Simplex Virus (HSV-1) transformed hamster cells with and without inoculation with $PDGF_2$.
Figure 6B:
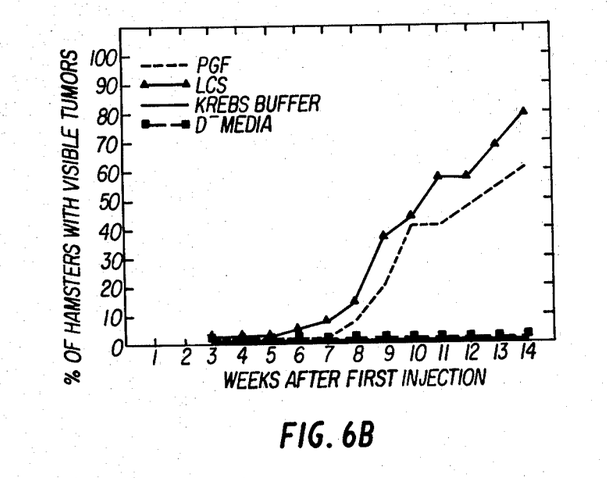

The above-described experiments have involved the in vitro stimulation of transformed cells with PDGF$_2$. Experiments have also been performed employing PDGF$_T$ and PDGF$_2$ to see if the growth of malignant cells in animals could be stimulated using this material. In these experiments, Herpes Simplex Virus (HSV-1) transformed hamster cells injected into golden Syrian hamsters were employed. As can be seen in FIG. 6, when PDGF$_T$ (or PDGF$_2$) is injected along with 100 HSV-1 transformed hamster cells into golden hamsters there is an acceleration of tumor cell growth. In control experiments at the end of 15 weeks none of the animals developed tumors. In animals that received both tumor cells and PDGF$_T$, 60% of the animals described grossly visible tumors by the end of the same period. It can be concluded that the transformed cell promoting factor present in human platelets can stimulate tumor growth both in vivo as well as in vitro.

Having now fully described the invention, it will be evident to one of ordinary skill in the art that many changes and modifications can be made thereto without departing from the spirit or scope of the invention as set forth herein.

What is claimed as new and desired to be secured by Letters Patent of the United States is:

1. A substantially purified glycoproteinaceous growth factor from platelets which has mitogenic activity toward transformed cells, a molecular weight of 3,000 to 5,000 daltons, a pI of 7.8–8.3, which is stable to treatment with 4 M guanidine hydrochloride, and which is heat labile when treated at 100° C. for 5 minutes, wherein said factor has mitogenic activity toward transformed cells selected from the group consisting of SV3T3, W8, and NQ-T-1 cell lines.

2. The factor of claim 1, wherein said platelets are human platelets.

3. A process for purifying the growth factor of claim 1 from platelets comprising:
   releasing from said platelets an extract containing said mitogenic activity;
   separating said platelets from said platelet extract;
   applying said platelet extract or a lypholyzed preparation thereof to a column comprising lectin or a cellulose-based ion exchanger;
   fractionally eluting said column;
   collecting fractions from said column that contain mitogenic activity.

4. The process of claim 3 wherein said salt solution is physiological saline.

5. The process of claim 3, wherein said extract is prepared by incubating said platelets with an isotonic salt solution at about 25 to 40° C. for at least approximately 10–30 minutes to form a platelet extract.

6. The process of claim 3 wherein said column is Con A-Sepharose and said eluting is with a glucose derivative.

7. The process of claim 6 wherein said derivative is methyl-$\alpha$-D-glucopyranoside.

8. The process of claim 3 wherein said column is DEAE Sephacel and said eluting is with a salt in solution.

9. The process of claim 8 wherein said salt is NaCl.

10. The process of claim 4 wherein said mitogenic activity is specific for transformed animal cells over non-transformed cells of the same species.

11. The process of claim 10 wherein said transformed animal cells are SV3T3 cells.

12. A method of promoting the growth of animal cells comprising contacting said cells with the factor of claim 1.

13. The method of claim 12, wherein said cells are transformed cells.

14. The method of claim 12, wherein said animal cells are mammalian cells.

15. The method of claim 12 or 13, wherein said growth is carried out in vitro.

16. The method of claim 12 or 13, wherein said growth occurs in vivo.

17. The process of claim 3 wherein said platelet extract is prepared by treating said platelets with thrombin, collagen, N-ethylmaleimide or arachldonic acid or by freezing and thawing said platelets.

* * * * *

UNITED STATES PATENT AND TRADEMARK OFFICE
CERTIFICATE OF CORRECTION

PATENT NO. : 4,350,687
DATED : September 21, 1982
INVENTOR(S) : ALLAN LIPTON ET AL It is certified that error appears in the above—identified patent and that said Letters Patent is hereby corrected as shown below:

In column 2, line 10, "100,00" should be --100,000--.

In column 3, line 31, "sephadex" should be --Sephadex--.

Column 4, line 60, delete "for" appearing immediately before the number "30".

Column 8, line 6, change "acxtivity" to --activity--.

Column 10, line 2 change "lypholyzed" to --lyophilized--.

Column 10, line 23, change "4" to --3--.

Column 10, line 41, change "arachldonic" to --arachidonic--.

Signed and Sealed this

Twenty-second Day of February 1983

[SEAL]

Attest:

Attesting Officer

GERALD J. MOSSINGHOFF

Commissioner of Patents and Trademarks